United States Patent
Boucher et al.

(10) Patent No.: US 7,722,624 B2
(45) Date of Patent: May 25, 2010

(54) EXPANDABLE STRUCTURES FOR DEPLOYMENT IN INTERIOR BODY REGIONS

(75) Inventors: Ryan P Boucher, San Francisco, CA (US); Mark A. Reiley, Piedmont, CA (US); Robert M. Scribner, Los Altos, CA (US); Karen D. Talmadge, Palo Alto, CA (US)

(73) Assignee: Kyphon SÀRL, Neuchatel (CH)

( * ) Notice: Subject to any disclaimer, the term of this patent is extended or adjusted under 35 U.S.C. 154(b) by 1218 days.

(21) Appl. No.: 10/784,392

(22) Filed: Feb. 23, 2004

(65) Prior Publication Data

US 2004/0167561 A1 Aug. 26, 2004
US 2007/0299460 A9 Dec. 27, 2007

Related U.S. Application Data

(60) Division of application No. 09/595,963, filed on Jun. 19, 2000, now Pat. No. 6,719,773, which is a continuation-in-part of application No. 09/420,529, filed on Oct. 19, 1999, now Pat. No. 6,607,544, which is a continuation-in-part of application No. 09/088,459, filed on Jun. 1, 1998, now abandoned, application No. 10/784,392, which is a continuation-in-part of application No. 09/827,260, filed on Apr. 5, 2001, now Pat. No. 6,726,691.

(51) Int. Cl.
 *A61B 17/58* (2006.01)
 *A61B 17/60* (2006.01)
 *A61F 2/00* (2006.01)

(52) U.S. Cl. .................. 606/105; 606/90; 606/92; 606/93; 606/94; 606/279

(58) Field of Classification Search .............. 606/53, 606/86, 90, 92–94, 194, 105; 600/18
See application file for complete search history.

(56) References Cited

U.S. PATENT DOCUMENTS

| | | | |
|---|---|---|---|
| 2,849,002 A | 8/1958 | Oddo | |
| 3,154,077 A | 10/1964 | Cannon | |
| 3,640,282 A | 2/1972 | Kamen et al. | |
| 3,648,294 A | 3/1972 | Shahrestani | |
| 3,779,239 A | 12/1973 | Fischer et al. | |
| 3,850,176 A | 11/1974 | Gottschalk | |
| 3,889,685 A | 6/1975 | Miller, Jr. et al. | |
| 4,083,369 A | 4/1978 | Sinnreich | |
| 4,261,339 A * | 4/1981 | Hanson et al. | 600/18 |
| 4,292,974 A | 10/1981 | Fogarty et al. | |
| 4,313,434 A | 2/1982 | Segal | |
| 4,327,736 A | 5/1982 | Inoue | |
| 4,338,942 A | 7/1982 | Fogarty | |

(Continued)

FOREIGN PATENT DOCUMENTS

EP 0 274 411 7/1988

(Continued)

*Primary Examiner*—Thomas C Barrett
*Assistant Examiner*—Andrew Yang
(74) *Attorney, Agent, or Firm*—Haynes and Boone, LLP

(57) ABSTRACT

An expandable structure carried at the end of a catheter tube assembly can be contracted and/or wrapped to present a reduced profile during deployment and/or removal from a targeted tissue site.

15 Claims, 9 Drawing Sheets

U.S. PATENT DOCUMENTS

| | | | |
|---|---|---|---|
| 4,402,307 A | 9/1983 | Hanson et al. | |
| 4,467,790 A * | 8/1984 | Schiff | 600/18 |
| 4,483,340 A * | 11/1984 | Fogarty et al. | 606/194 |
| 4,531,512 A | 7/1985 | Wolvek et al. | |
| 4,848,344 A | 7/1989 | Sos et al. | |
| 4,917,088 A | 4/1990 | Crittenden | |
| 4,969,888 A * | 11/1990 | Scholten et al. | 606/94 |
| 4,983,167 A | 1/1991 | Sahota | |
| 5,102,390 A * | 4/1992 | Crittenden et al. | 604/103.1 |
| 5,104,376 A | 4/1992 | Crittenden | |
| 5,108,404 A | 4/1992 | Scholten et al. | |
| 5,163,989 A | 11/1992 | Campbell et al. | |
| 5,254,091 A | 10/1993 | Aliahmad et al. | |
| 5,295,994 A | 3/1994 | Bonutti | |
| 5,352,199 A | 10/1994 | Tower | |
| 5,415,635 A | 5/1995 | Bagaoisan et al. | |
| 5,439,447 A | 8/1995 | Miraki | |
| 5,468,245 A | 11/1995 | Vargas, III | |
| 5,480,400 A | 1/1996 | Berger | |
| 5,500,181 A | 3/1996 | Wang et al. | |
| 5,587,125 A | 12/1996 | Roychowdhury | |
| 5,728,063 A | 3/1998 | Preissman et al. | |
| 5,741,282 A | 4/1998 | Ansach, III et al. | |
| 5,766,151 A | 6/1998 | Valley et al. | |
| 5,827,289 A | 10/1998 | Reiley et al. | |
| 5,938,582 A | 8/1999 | Ciamacco et al. | |
| 5,972,015 A | 10/1999 | Scribner et al. | |
| 6,048,346 A | 4/2000 | Reiley | |
| 6,066,154 A | 5/2000 | Reiley et al. | |
| D439,980 S | 4/2001 | Reiley et al. | |
| 6,235,043 B1 | 5/2001 | Reiley | |
| 6,241,734 B1 | 6/2001 | Scribner et al. | |
| 6,248,110 B1 | 6/2001 | Reiley et al. | |
| 6,379,373 B1 | 4/2002 | Sawhney et al. | |
| 6,383,212 B2 | 5/2002 | Durcan et al. | |
| 6,423,083 B2 | 7/2002 | Reiley et al. | |
| 6,726,691 B2 * | 4/2004 | Osorio et al. | 606/94 |

FOREIGN PATENT DOCUMENTS

| | | |
|---|---|---|
| EP | 0 597 465 | 9/1988 |
| EP | 0 135 990 | 9/1990 |
| EP | 0 410 072 | 1/1991 |
| EP | 0 436 501 | 4/1993 |
| EP | 0 420 488 | 7/1993 |
| EP | 0 439 202 | 9/1993 |
| EP | 0 592 885 | 9/1993 |
| EP | 0 318 919 | 1/1994 |
| EP | 0 383 794 | 6/1994 |
| EP | 0 355 937 | 11/1995 |
| EP | 0 713 712 | 5/1996 |
| EP | 0 730 879 | 9/1996 |
| EP | 0 531 117 | 1/1997 |
| EP | 0 362 826 | 5/1997 |
| EP | 0 566 684 | 6/1997 |
| EP | 0 779 062 | 6/1997 |
| EP | 0 826 395 | 3/1998 |
| EP | 0 834 293 | 4/1998 |
| JP | 8038618 | 2/1996 |
| WO | WO 89/02763 | 4/1989 |
| WO | WO 91/17788 | 11/1991 |
| WO | WO 92/11892 | 7/1992 |
| WO | WO 92/19440 | 11/1992 |
| WO | WO 94/02197 | 2/1994 |
| WO | WO 95/20362 | 8/1995 |
| WO | WO 95/22367 | 8/1995 |
| WO | WO 96/04951 | 2/1996 |
| WO | WO 96/12516 | 5/1996 |
| WO | WO 96/39970 | 12/1996 |
| WO | WO 97/03716 | 2/1997 |
| WO | WO 97/17098 | 5/1997 |
| WO | WO 97/17099 | 5/1997 |
| WO | WO 97/40877 | 11/1997 |
| WO | WO 98/03218 | 1/1998 |
| WO | 9856301 | 12/1998 |
| WO | WO 98/56301 | 12/1998 |
| WO | WO 99/29246 | 6/1999 |
| WO | WO 99/37212 | 7/1999 |
| WO | WO 99/51149 | 10/1999 |
| WO | WO 99/62416 | 12/1999 |
| WO | WO 01/28439 | 4/2001 |
| WO | WO 01/76514 | 10/2001 |

* cited by examiner

EXPANDABLE STRUCTURES FOR DEPLOYMENT IN INTERIOR BODY REGIONS

RELATED APPLICATIONS

This application is a divisional of U.S. patent application Ser. No. 09/595,963, filed Jun. 19, 2000 (now U.S. Pat. No. 6,719,773), which is a continuation-in-part of U.S. patent application Ser. No. 09/420,529, filed Oct. 19, 1999, and entitled "Expandable Preformed Structures for Deployment in Interior Body Regions," now U.S. Pat. No. 6,607,544, and which is also a continuation-in-part of U.S. patent application Ser. No. 09/088,459, filed Jun. 1, 1998, and entitled "Expandable Preformed Structures for Deployment in Interior Body Regions, now abandoned." This application is also a continuation-in-part of U.S. patent application Ser. No. 09/827,260, filed Apr. 5, 2001, and entitled Methods for Treating Fractured and/or Diseased Bone (now U.S. Pat. No. 6,726,691).

FIELD OF THE INVENTION

The invention relates to expandable structures, which, in use, are deployed in interior body regions of humans and other animals.

BACKGROUND OF THE INVENTION

The deployment of expandable structures, sometimes generically called "balloons," into cancellous bone is known. For example, U.S. Pat. Nos. 4,969,888 and 5,108,404 disclose apparatus and methods using expandable structures to compact cancellous bone for the fixation of fractures or other osteoporotic and non-osteoporotic conditions of human and animal bones.

In these and other clinical indications, it is desirable to use tissue insertion and deployment tools that are small, so that access to the targeted tissue site can be achieved using minimally invasive procedures. Still, it is also desirable to deploy structures that, in use within the targeted tissue site, are capable of assuming enlarged, durable shapes, so that cortical bone can be displaced in a desired manner and/or large cavities can be created in cancellous bone without over-expansion, puncture, and/or abrasion of the structure.

There is a need to meet the demand for small insertion tools without conflicting with the objective to deploy large expandable structures.

SUMMARY OF THE INVENTION

The invention provides systems and methods that permit expandable, large, durable structures to be deployed through small, minimally invasive accesses.

One aspect of the invention provides a tool for treating bone. The tool comprises a structure having opposite ends spaced along an axis. The structure is adapted to be inserted into bone and undergo expansion outwardly about the axis in cancellous bone and/or against cortical bone. The tool includes a wrapping mechanism coupled to the structure. The wrapping mechanism wraps the structure inwardly about the axis, to reduce its outside diameter to facilitate its insertion into bone.

In one embodiment, the wrapping mechanism is operable to impart a force to stretch the structure along the axis.

In one embodiment, the wrapping mechanism is operable to impart a force to stretch the structure along the axis while wrapping the structure inwardly about the axis.

In one embodiment, the wrapping mechanism is operable to affect differential rotation of one end of the structure about the axis relative to the other end, thereby wrapping the structure inwardly about its axis.

In one embodiment, the opposite ends of the structure comprise a proximal end and a distal end. In one arrangement, the wrapping mechanism affects differential rotation of the distal end relative to the proximal end. In another arrangement, the wrapping mechanism affects differential rotation of the proximal end relative to the distal end.

In one embodiment, a proximal end of the structure is carried by a catheter tube. In this arrangement, the wrapping mechanism is coupled to a distal end of the structure to rotate the distal structure end about the axis while the proximal structure end is held substantially free of rotation by the catheter tube.

In one embodiment the wrapping mechanism includes an actuator carried on the proximal end of a catheter tube, the distal end of which carries the structure.

In one embodiment, a proximal end of the structure is carried at the distal end of a catheter tube. The wrapping mechanism includes a stylet rotatable within the catheter tube having a far end coupled to the distal end of the structure. In this arrangement, an actuator on the proximal end of the catheter tube is coupled to a near end of the stylet to rotate the stylet within the catheter tube. Rotation of the stylet, in turn, affects rotation of the distal end of the structure while the proximal end of the structure is held substantially free of rotation by the distal end of the catheter tube.

In one embodiment, the wrapping mechanism includes an element that imposes a force to resist unwrapping of the structure.

In one embodiment, the structure includes material that, during expansion in cancellous bone, applies a force capable of moving fractured cortical bone.

In one embodiment, the structure includes material to constrain expansion in cancellous bone.

In one embodiment, the structure includes material that expands directly against cortical bone to displace the cortical bone in a desired direction.

In one embodiment, the structure includes an elastomer material having a region preformed with a normally expanded shape outside bone.

In one embodiment, the structure comprises a stop which prevents and/or inhibits the structure from being advanced into the bone beyond a predetermined depth.

Another aspect of the invention provides a method for treating bone. The method provides a structure having opposite ends spaced along an axis. The structure is adapted to undergo expansion outwardly about the axis.

The structure possesses a normally unwrapped condition having an outside diameter. The method places the structure in a wrapped condition by wrapping the structure inwardly about the axis to reduce the outside diameter. The method inserts the structure, while in the wrapped condition, into bone. The structure returns to the unwrapped condition inside bone and causes expansion of the structure in cancellous bone.

In one embodiment, the method includes the step of introducing a material into the bone.

In one embodiment, the step of expansion moves cortical bone.

In one embodiment, the method includes, after the expansion step, the step of reducing the size of the structure for removal from the bone. In one arrangement, the reducing step includes placing the structure in the wrapped condition.

In an alternate embodiment, the method comprises reducing the size of the structure for removal from the bone. In one arrangement, the reducing step includes placing the structure in the wrapped condition.

In one embodiment, the wrapping step includes causing differential rotation of one end of the structure about the axis relative to the other end.

Features and advantages of the inventions are set forth in the following Description and Drawings, as well as in the appended claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

The preferred embodiment describes improved systems and methods that embody features of the invention in the context of treating bones. This is because the systems and methods can be advantageously applied for this purpose. However, aspects of the invention can be advantageously applied for diagnostic or therapeutic purposes in other areas of the body.

The systems and methods will be more specifically described in the context of the treatment of human vertebra. Of course, other human or animal bone types can be treated in the same or equivalent fashion. By way of example, and not by limitation, the present systems and methods could be used in any bone having bone marrow therein, including the radius, the humerus, the vertebrae, the femur, the tibia or the calcaneus.

I. Anatomy of a Vertebral Body

Figure 1:
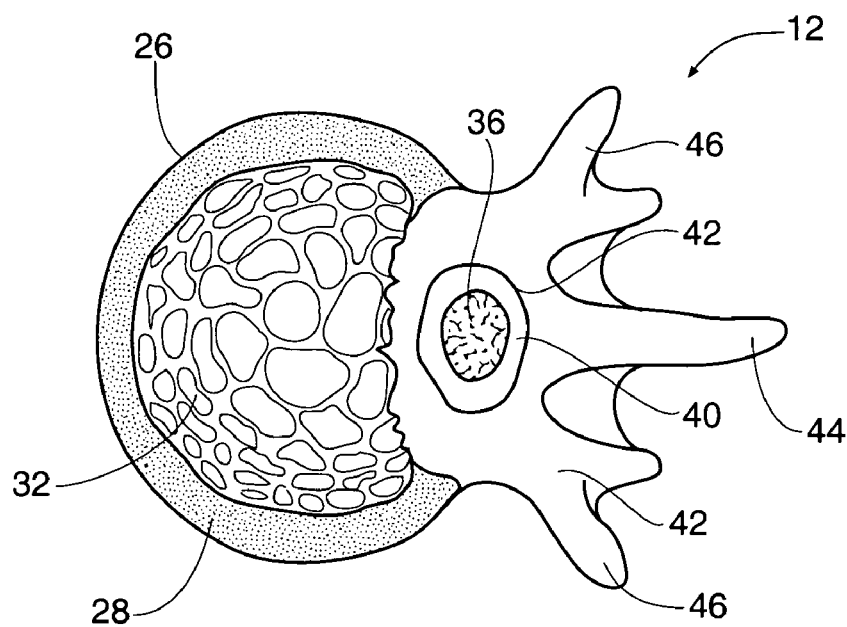
FIG. 1 is a coronal view of a vertebral body.
Figure 2:
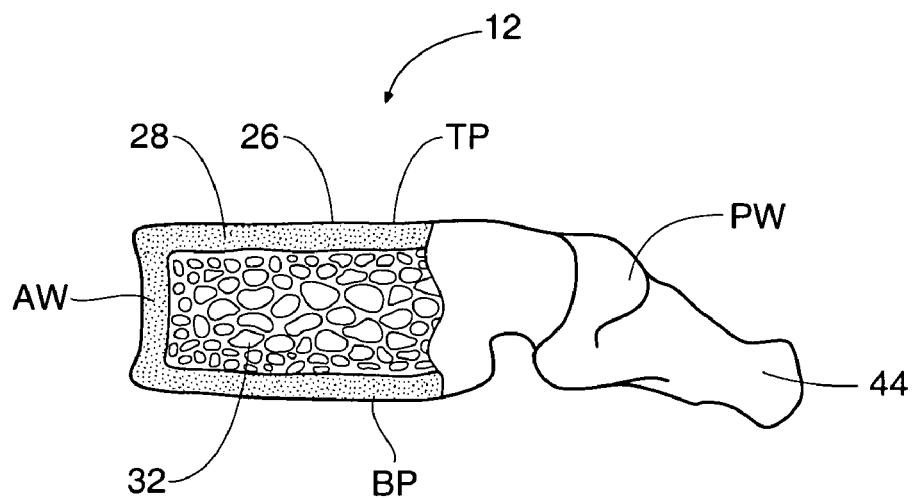
FIG. 2 is a lateral view of the vertebral body shown in FIG. 1.

FIG. 1 shows a coronal (top) view of a human lumbar vertebra 12. FIG. 2 shows a lateral (side) view of the vertebra 12. The vertebra 12 includes a vertebral body 26, which extends on the anterior (i.e., front or chest) side of the vertebra 12. The vertebral body 26 is shaped generally like a hockey puck.

As FIGS. 1 and 2 show, the vertebral body 26 includes an exterior formed from compact cortical bone 28. The cortical bone 28 encloses an interior volume of reticulated cancellous, or spongy, bone 32 (also called medullary bone or trabecular bone).

The spinal canal 36 (see FIG. 1), is located on the posterior (i.e., back) side of each vertebra 12. The spinal cord (not shown) passes through the spinal canal 36. The vertebral arch 40 surrounds the spinal canal 36. Left and right pedicles 42 of the vertebral arch 40 adjoin the vertebral body 26. The spinous process 44 extends from the posterior of the vertebral arch 40, with the left and right transverse processes 46 extending from the sides of the vertebral arch.

It may be indicated, due to disease or trauma, to compress cancellous bone within the vertebral body. The compression, for example, can be used to form an interior cavity, which receives a filling material, e.g., a flowable material that sets to a hardened condition, like bone cement, allograft tissue, autograft tissue, hydroxyapatite, or synthetic bone substitute, as well as a medication, or combinations thereof, to provide improved interior support for cortical bone or other therapeutic functions, or both. The compaction of cancellous bone may also exert interior force upon cortical bone, making it possible to elevate or push broken and compressed bone back to or near its original prefracture, or other desired, condition.

Alternatively, it may be indicated to move cortical bone, with or without concurrent compaction of cancellous bone. The present system and methods can be utilized to directly and/or indirectly displace cortical bone in one or more desired directions.

II. Tool for Treating Vertebral Bodies

Figure 3:
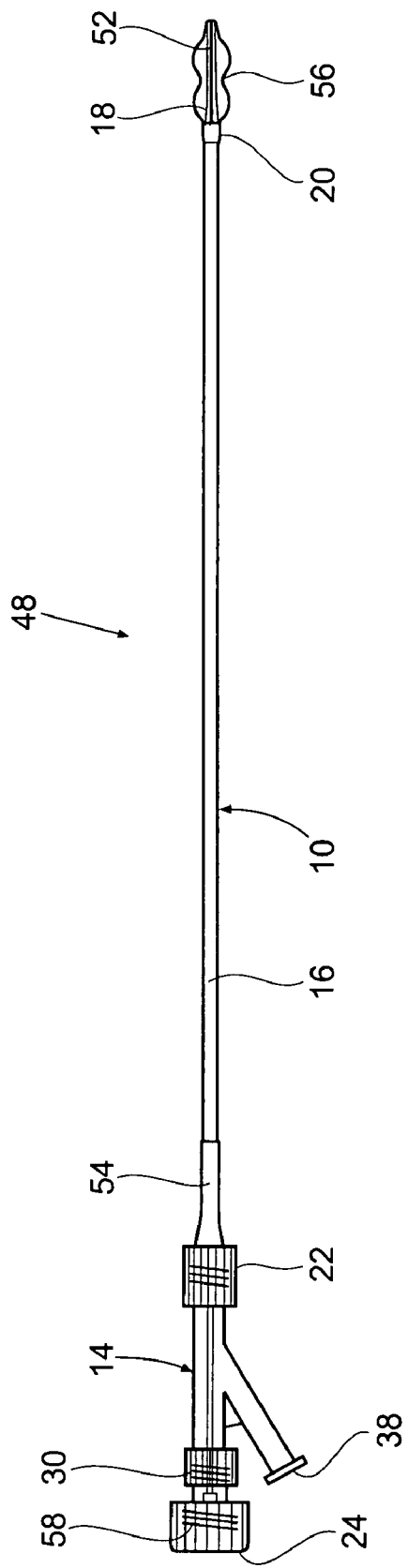
FIG. 3 is a plan view of a tool which carries at its distal end an expandable structure that embodies features of the invention.
Figure 4:
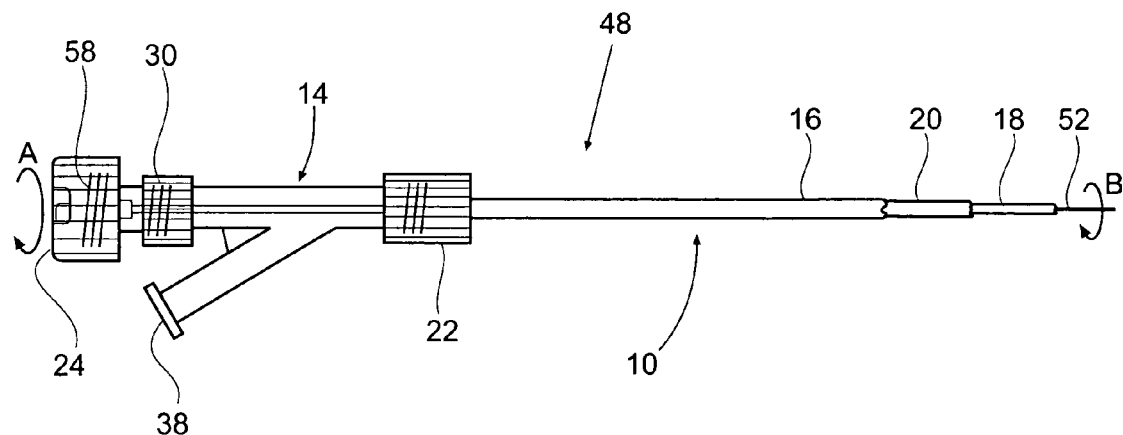
FIG. 4 is an enlarged view of the proximal end of the tool shown in FIG. 3, showing the three part catheter tube assembly, stylet, and their connection to a handle.
Figure 5:
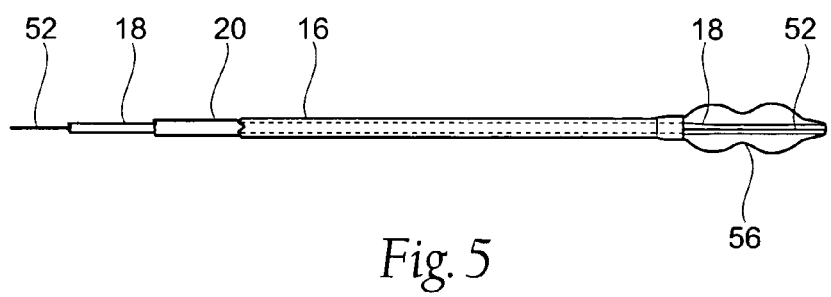
FIG. 5 is an enlarged view of the distal end of the tool shown in FIG. 3, showing the three part catheter tube assembly, stylet, and their connection to the expandable structure.

FIGS. 3 to 5 show a tool 48 for compacting cancellous bone, creating a cavity within the bone and/or displacing cortical bone. The tool 48 includes a catheter tube assembly 10 made, e.g., from metal or extruded plastic materials. If desired, the catheter tube can be generally flexible. The distal end of the catheter tube assembly 10 carries an expandable structure 56, which is made, e.g., from a deformable plastic or metal material. Further details of the physical and mechanical properties of the material for the catheter tube assembly 10 and expandable structure 56 will be described later. In use, the structure 56 is deployed and expanded inside bone, e.g., in the vertebral body 26 shown in FIGS. 1 and 2, to compact cancellous bone 32 and/or displace cortical bone, as will also be described later.

As best shown in FIGS. 4 and 5, the catheter tube assembly 10 includes an outer catheter body 16, a middle catheter body 20, and an inner catheter body 18. The middle catheter body 20 extends through the outer catheter body 16. The inner catheter body 18 extends through the middle catheter body 20.

Figure 7:
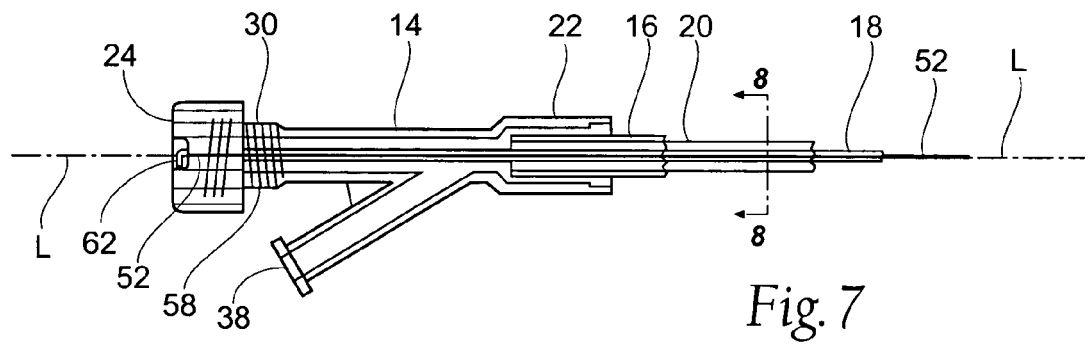
FIG. 7 is a further enlarged view of the proximal end of the tool shown in FIG. 4, showing further details of the connection between the three part catheter tube assembly, stylet, and handle.

As best shown in FIG. 7, the proximal end of the middle catheter body 20 is coupled to the proximal end of the outer catheter body 16. The coupled proximal ends of the outer and middle catheter bodies 16 and 20 are, in turn, jointly coupled to the distal end of a luer fitting 22 on a y-shaped adapter 14, which serves as a handle for the tool 48.

As FIG. 7 also shows, the proximal end of the inner catheter body 18 extends within the adapter 14 beyond the coupled proximal ends of the outer and middle catheter bodies 16 and 20. The extended proximal end of the inner catheter body 18 is coupled to the y-shaped handle adapter 14 at a location proximal to an inflation port 38.

Figure 6:
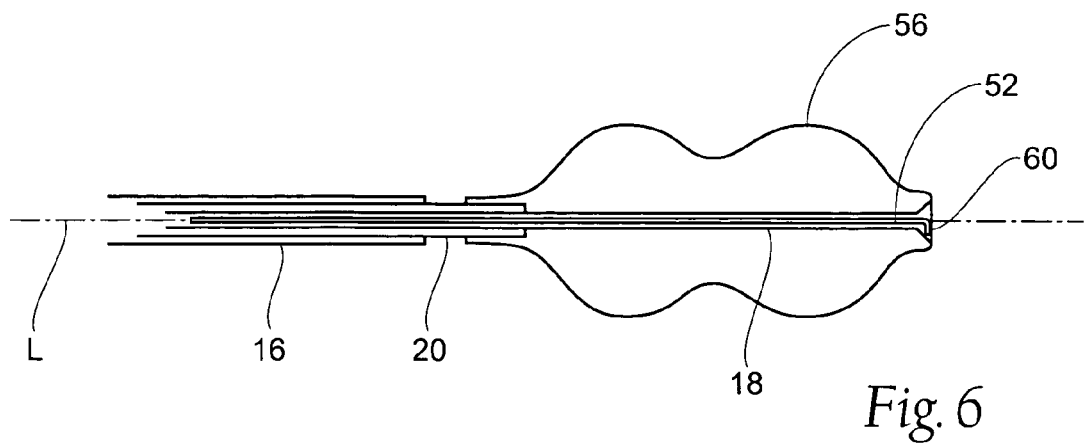
FIG. 6 is a further enlarged view of the distal end of the tool shown in FIG. 5, showing further details of the connection between the three part catheter tube assembly, stylet, and expandable structure.

As FIG. 6 shows, the distal end of the inner catheter body 18 extends beyond the distal end of the middle catheter body 20. As FIG. 6 also shows, the expandable structure 56 is coupled at its distal end to the distal end of the inner catheter body 18. The expandable structure 56 is coupled at its proximal end to the distal end of the middle catheter body 20. The distal end of the outer catheter body 16 is coupled to the middle catheter body 20 adjacent to the junction of the expandable structure 56 and the middle catheter body 20.

Figure 8:
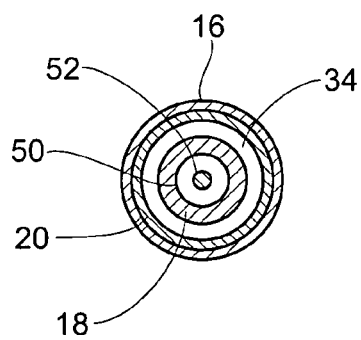
FIG. 8 is a sectional view of the three part catheter tube assembly and stylet taken generally along line 8-8 in FIG. 7.

As FIG. 8 shows, the interior diameter of the middle catheter body 20 is larger than the exterior diameter of the inner catheter body 18. An interior passage 34 is thereby defined between them. In use, the interior passage 34 conveys a pressurized flowable medium, e.g., sterile water, radiopaque fluid (such as CONRAY™ solution, from Mallinkrodt, Inc.), gas, or other flowable substance into the structure 56, to expand it. The inflation port 38 on the handle 14 (see, e.g., FIG. 7) serves, in use, to couple the interior passage 34 to the source of pressurized flowable medium (not shown).

The inner catheter body 18 itself defines an interior lumen 50 (see FIG. 8) within the interior passage 34. A generally flexible, torque transmitting stylet 52 made, e.g., from metal or plastic, extends through the interior lumen 50. As FIG. 6 best shows, the distal end of the stylet 52 is jointly coupled with the distal end of the inner catheter body 18 to the distal end of the expandable structure 56.

As FIG. 7 shows, the proximal end of the stylet 52 is coupled to a rotatable luer cap 24. The luer cap 24 rotates on threads 58 about the proximal luer fitting 30 on the y-shaped adapter/handle 14. Twisting the luer cap 24 on the threads 58 (arrow A in FIG. 4) rotates the stylet 52 within the inner catheter body 18 (arrow B in FIG. 4). The proximal ends of the middle catheter body 20 and outer catheter body 16 desirably remain substantially stationary, and do not rotate significantly with the stylet 52.

The torque caused by twisting the luer cap 24 is transmitted by the stylet 52 to the distal ends of inner catheter body 18 and the expandable structure 56, which, as before described, are jointly coupled to the distal end of the stylet 52. The proximal end of the expandable structure 56, being coupled to the substantially stationary middle catheter body 20, desirably remains stationary.

As the luer cap 24 is rotated in the direction of the threads 58 (which is clockwise in the drawings, shown by arrow A in FIG. 9), the distal end of the expandable structure 56 rotates in the same direction (shown by arrow B in FIG. 9) while the proximal end of the expandable structure 56 desirably remains substantially stationary.

It should be appreciated that the proximal end of the structure 56 need not remain substantially stationary to accomplish one or more goals of the invention. Rather, it is the differential rotation of the proximal and distal ends of the structure 56 that desirably wraps the structure 56 to some degree. For example, if the middle catheter body 20 and/or outer catheter body 16 deformed during rotation of the stylet 52, allowing the proximal end of the structure 56 to rotate, the differences in rotation between the distal and proximal ends of the structure 56 would still desirably "wrap" the structure 56 to some degree. In a similar manner, if some portion of the structure were rotated relative to another portion of the structure, and the distal and proximal ends of the structure remained substantially stationary relative to each other, the structure would still desirably "wrap" to some degree.

Similarly, if the stylet 52 were substantially motionless and the proximal end of the catheter tube assembly 10 were rotated, the structure 56 would also "wrap." Desirably, in this arrangement, the proximal end of the structure 56 will rotate at least one-third (⅓rd) of a complete rotation relative to the distal end of the structure 56. More desirably, the proximal end of the structure 56 will rotate at least one complete rotation relative to the distal end of the structure. Even more desirably, the proximal end of the structure will rotate at least two complete rotations relative to the distal end of the structure 56. Most desirably, the proximal end of the structure 56 will rotate at least three complete rotations relative to the distal end of the structure 56.

Figure 9:
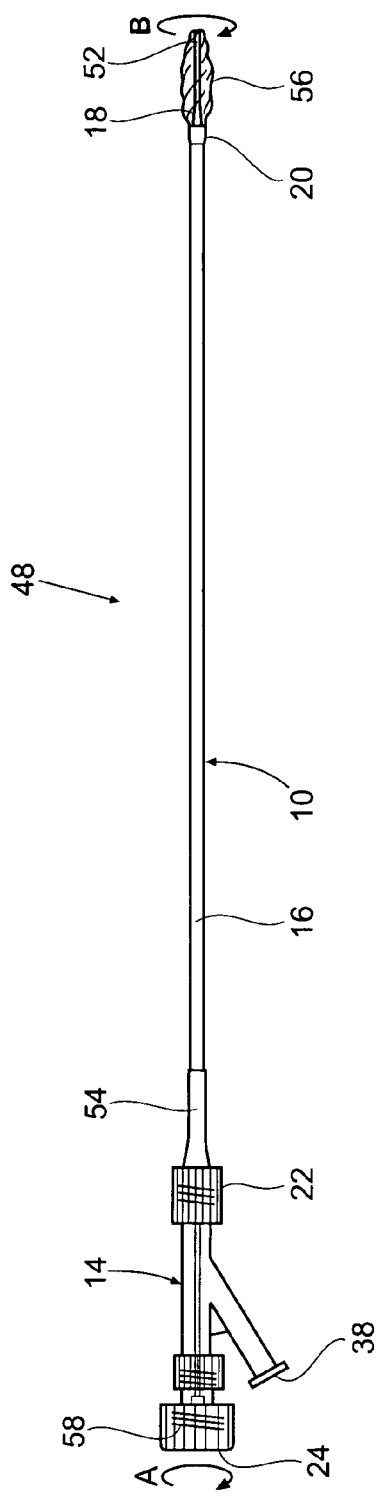
FIG. 9 is a plan view of the tool shown in FIG. 3, with the expandable structure in a partially twisted and wrapped condition caused by rotation of the stylet within the catheter tube assembly.
Figure 10:
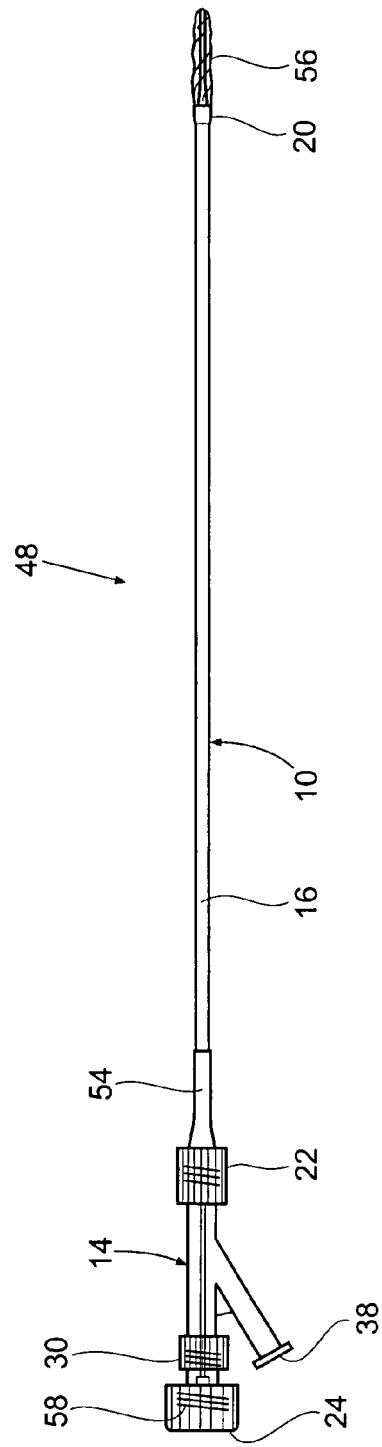
FIG. 10 is a plan view of the tool shown in FIG. 3, with the expandable structure in a fully twisted and wrapped condition caused by rotation of the stylet within the catheter tube assembly.

As FIGS. 9 and 10 show, the resulting rotational force transmitted by the stylet 52 progressively twists the distal end of the structure 56 relative to the proximal end of the structure 56. As FIGS. 9 and 10 shows, the progressive twisting wraps the structure 56 inwardly about the distal end of the inner catheter body 18. Desirably, this wrapping action also distributes the structure uniformly around the inner catheter body.

As FIGS. 9 and 10 show, the wrapping progressively reduces the outside diameter of the structure 56. When fully wrapped about the inner catheter body 18 (as FIG. 10 depicts), the outside diameter of the structure 56 desirably approximates or is less than the inside diameter of the cannula 78 (see FIG. 11). Similarly, because the inner catheter body 18 is secured to both the y-shaped adapter 14 and the distal end of the stylet 52, the rotation of the stylet 52 will also desirably "twist" the inner catheter body 18, desirably reducing the outside diameter of the inner catheter body 18 and further reducing the overall outside diameter of the structure 56.

The threads 58 desirably impose a frictional drag, which resists the counter resilience of the material of the structure 56 tending to unwrap the wrapped structure 56. The frictional drag keeps the structure 56 within a range of wrapped conditions (see FIG. 9) in the absence of rotational force applied to the luer cap 24. Of course, other devices, such as magnetic or frictional locks or detent mechanisms, could be used to secure the structure 56 in a wrapped, partially-wrapped and/or unwrapped condition.

In the disclosed embodiment, the movement of the luer cap 24 along the longitudinal axis L of the tool 48, also longitudinally stretches and/or radially shrinks the structure 56, further reducing the overall outside diameter. For example, as the luer cap 24 rotates clockwise, the luer cap 24 moves toward the distal luer fitting 22 along the longitudinal axis L. The stylet 52, which is secured to the luer cap 24, is similarly displaced along the longitudinal axis L, which in turn displaces the distal end of the expandable structure 56.

This displacement increases the longitudinal length of the structure 56, which "stretches" the expandable structure 56, further drawing the structure 56 against the inner catheter body 18 and/or causing a thinning of the structure 56. This also desirably reduces the outside diameter of the structure 56.

If desired, the threads can be reversed, such that clockwise rotation of the luer cap 24 causes the luer cap 24 to move away from the distal luer fitting 22. In this alternative arrangement, clockwise rotation of the luer cap 24 would allow the longitudinal length of the structure to shorten as it wraps about the inner catheter body 18.

Rotation of the luer cap 24 in the opposite direction, which is counterclockwise in the drawings, causes the structure 56 to unwrap from about the inner catheter body 18, returning to its normal outside diameter for use (as shown in FIG. 3).

The tool 48 can also include an insertion sleeve 54 (see FIG. 3). The insertion sleeve 54 desirably slides along the outer catheter body 16. The insertion sleeve 54 can be slid forward over the wrapped structure 56, to protect the structure 56 and/or aid insertion of the structure 56 into a cannula 78. Once the structure 56 is deployed into the cannula 78, the insertion sleeve 54 can be slid aft away from the structure 56, and can, if desired, engage the handle 14 during further use of the tool 48.

Figure 14:
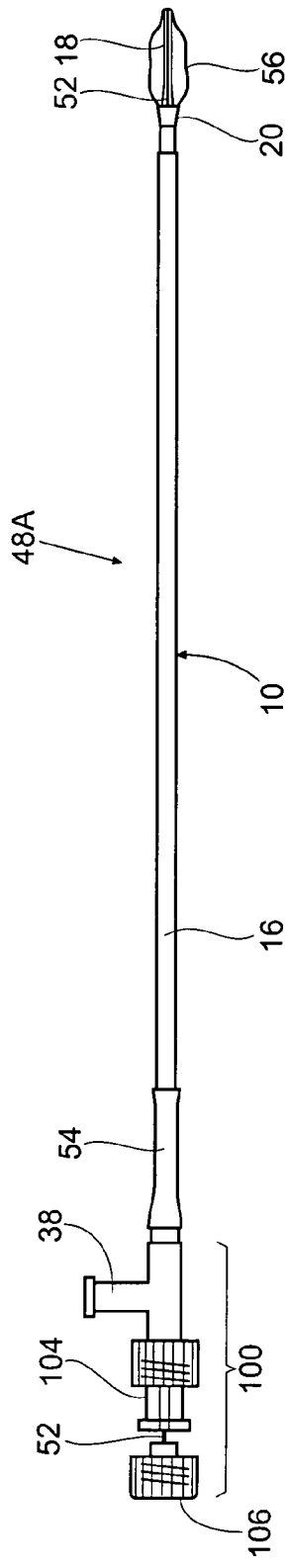
FIG. 14 is a plan view of an alternative embodiment of a tool which carries at its distal end an expandable structure that embodies features of the invention.

FIG. 14 shows an alternative embodiment of a tool 48A for compacting cancellous bone, creating a cavity within bone and/or displacing cortical bone, which embodies features of the invention. Because many structural components of the tool 48A are similar to those of the tool 48, like reference numerals will be used to identify like components.

In this embodiment, the proximal ends of the outer, middle, and inner catheter bodies 16, 20, and 18 are coupled to a t-shaped adapter 100. The proximal end of the stylet 52 is coupled to a luer cap 106. Desirably, the luer cap 106 will be spaced apart from a corresponding luer fitting 104 when the structure 56 is unstretched and/or untwisted. In the disclosed embodiment, the luer cap 106 is spaced approximately one-fourth (¼th) inches from the luer fitting 104, although this spacing could be increased or decreased, depending upon the length of the stylet 52 and the amount of stretching desired for the structure 56.

When the tool 48A is prepared for deployment, the luer cap 106 is desirably pushed longitudinally towards the luer fitting 104 so that it contacts the luer fitting 104. This desirably elongates the structure 56 and reduces its overall outside diameter. The luer cap 106 is then engaged with the luer fitting 104. If desired, the luer cap 106 and luer fitting 106 can engage by twisting, which will twist the structure and further reduce the overall outside diameter. Alternatively, the luer cap 106 and luer fitting could be a snap-lock type fitting.

Figure 15:
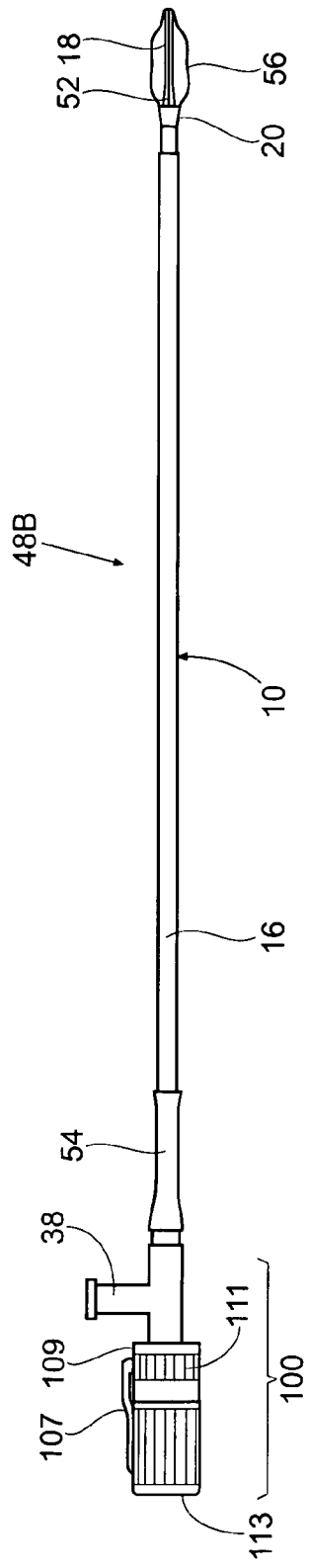
FIG. 15 is a plan view of another alternative embodiment of a tool which carries at its distal end an expandable structure that embodies features of the invention.

FIG. 15 shows another alternative embodiment of a tool 48B for compacting cancellous bone, creating a cavity within bone and/or displacing cortical bone, which embodies features of the invention. As in FIG. 14, because many of the structural components of the tool 48B are similar to those of the tool 48, like reference numerals will be used to identify like components.

In this embodiment, the proximal ends of the outer, middle and inner catheter bodies 16, 20 and 18 are coupled to a t-shaped adapter 100. The t-shaped adapter 100 comprises a stationary fitting 109, a rotatable fitting 113, and an automatic or manually operated detent mechanism 107. One or more notches 111 are disposed on the stationary fitting 109. The proximal end of the stylet 52 is desirably coupled to the rotatable fitting 113.

When the tool 48B is prepared for deployment, the detent mechanism 107 can be disengaged from the one or more notches 111, and the rotatable fitting 113 rotated, which desirably twists the structure 56 and reduces its overall outside diameter. The detent mechanism 107 is then engaged to secure the structure 56 in its low profile position for insertion into the cannula. If desired, the detent mechanism 107 can incorporate threads or other devices which advance/withdraw the stylet 52 in response to rotation of the rotatable fitting.

Various materials can be selected for the component parts of the tool 48. Furthermore, the dimensions of the component parts of the tool 48 can also vary, according to its intended use. The following table lists preferred component materials and dimensions, which are well suited for a tool 48 that can be deployed for use in a vertebral body:

| Component | Material | Dimension (Inches) |
| --- | --- | --- |
| Outer catheter body 16 | TEXIN ® 5270 Polyurethane | Outside Diameter: 0.124 Inside Diameter: 0.102 |
| Middle Catheter body 20 | TEXIN ® 5270 Polyurethane | Outside Diameter: 0.078 Inside Diameter 0.054 |
| Inner Catheter Body 18 | TEXIN ® 5270 Polyurethane | Outside Diameter: 0.035 Inside diameter: 0.025 |
| Expandable Structure | TEXIN ® 5286 Polyurethane | As formed: Axial Length (from distal end of middle catheter tube to distal end of inner catheter tube): 0.949 Wrapped Diameter: 0.124 Normal Non-Expanded Diameter: 0.270 |
| Tool | | Total end to end length: 15.75 |
| Stylet | Stainless Steel | Outside Diameter: 0.023 |
| Insertion Sleeve 54 | PEBAX ® Tubing | Outside Diameter: 0.172" Inside Diameter: 0.140 Length: 1.5 |

The component parts of the tool 48 can be formed and assembled in various ways. A preferred assembly will now be described.

A. The Expandable Structure

The material from which the structure 56 is made 10 should possess various physical and mechanical properties to optimize its functional capabilities to compact cancellous bone. Important properties for the structure include one or more of the following: (1) the ability to expand in volume; (2) the ability to deform in a desired way when expanding and assume a desired shape inside bone; and/or (3) the ability to withstand abrasion, tearing, and puncture when in contact with cancellous and/or cortical bone.

1. Expansion Property

A first desired property for the structure material is the ability to expand or otherwise increase in volume without failure. This property enables the structure 56 to be deployed in a collapsed, low profile condition subcutaneously, e.g., through a cannula, into the targeted bone region. This property also enables the expansion of the structure 56 inside the targeted bone region to press against and compress surrounding cancellous bone, or move cortical bone to a prefracture or other desired condition, or both.

The desired expansion property for the structure material can be characterized in one way by ultimate elongation properties, which indicate the degree of expansion that the material can accommodate prior to failure. Sufficient ultimate elongation permits the structure 56 to compact cortical bone, as well as lift contiguous cortical bone, if necessary, prior to wall failure. Desirably, the structure 56 will comprise material able to undergo an ultimate elongation of at least 50%, prior to wall failure, when expanded outside of bone. More desirably, the structure will comprise material able to undergo an ultimate elongation of at least 150%, prior to wall failure, when expanded outside of bone. Most desirably, the structure will comprise material able to undergo an ultimate elongation of at least 300%, prior to wall failure, when expanded outside of bone.

Alternatively, the structure material can comprise one or more non-compliant or partially compliant materials having substantially lower ultimate elongation properties, including, but not limited to, kevlar, aluminum, nylon, polyethylene, polyethyiene-terephthalate (PET) or mylar. Such a structure would desirably be initially formed to a desired shape and volume, and then contracted to a collapsed, low profile condition for introduction through a cannula into the targeted bone region. The structure could then be expanded to the desired shape and volume to press against and compress surrounding cancellous bone and/or move cortical bone to a prefracture or desired condition, or both. As another alternative, the structure could comprise a combination of non-compliant, partially compliant and/or compliant materials.

2. Shape Property

A second desired property for the material of the structure 56, either alone or in combination with the other described properties, is the ability to predictably deform during expansion, so that the structure 56 consistently achieves a desired shape inside bone.

The shape of the structure 56, when expanded in bone, is desirably selected by the physician, taking into account the morphology and geometry of the site to be treated. The shape of the cancellous bone to be compressed and/or cortical bone to be displaced, and the local structures that could be harmed if bone were moved inappropriately, are generally understood by medical professionals using textbooks of human skeletal anatomy along with their knowledge of the site and its disease or injury, and also taking into account the teachings of U.S. patent application Ser. No. 08/788,786, filed Jan. 23, 1997, and entitled "Improved Inflatable Device for Use in Surgical Protocol Relating to Fixation of Bone," which is incorporated herein by reference. The physician is also desirably able to select the desired expanded shape inside bone based upon prior analysis of the morphology of the targeted bone using, for example, plain film x-ray, fluoroscopic x-ray, or MRI or CT scanning.

Where compression of cancellous bone and/or cavity creation is desired, the expanded shape inside bone is selected to optimize the formation of a cavity that, when filled with a selected material, provides support across the region of the bone being treated. The selected expanded shape is made by evaluation of the predicted deformation that will occur with increased volume due to the shape and physiology of the targeted bone region.

Where displacement of cortical bone is desired, the expanded shape can be selected to optimize displacement of the cortical bone in the desired direction(s), as well as to distribute forces in a desired manner across the targeted cortical bone region. If desired, the structure can be designed to distribute forces evenly and/or uniformly across the targeted cortical bone region. Alternatively, the structure can be designed to impart a maximum force on a specific area of the cortical bone so as to cause desired fracture and/or maximum displacement of specific cortical bone regions.

In some instances, it is desirable, when creating a cavity, to also move or displace the cortical bone to achieve the desired therapeutic result. Such movement is not per se harmful, as that term is used in this Specification, because it is indicated to achieve the desired therapeutic result. By definition, harm results when expansion of the structure 56 results in a worsening of the overall condition of the bone and surrounding anatomic structures, for example, by injury to surrounding tissue or causing a permanent adverse change in bone biomechanics.

As one general consideration, in cases where the bone disease causing fracture (or the risk of fracture) is the loss of cancellous bone mass (as in osteoporosis), the selection of the expanded shape of the structure 56 inside bone should take into account the cancellous bone volume which should be compacted to achieve the desired therapeutic result. An exemplary range is about 30% to 90% of the cancellous bone volume, but the range can vary depending upon the targeted bone region. Generally speaking, compacting less of the cancellous bone volume leaves more uncompacted, diseased cancellous bone at the treatment site.

Another general guideline for the selection of the expanded shape of the structure 56 inside bone is the amount that the targeted fractured bone region has been displaced or depressed. The expansion of the structure 56 inside a bone can elevate or push the fractured cortical wall back to or near its anatomic position occupied before fracture occurred.

For practical reasons, it is often desired that the expanded shape of the structure 56 inside bone, when in contact with cancellous bone, substantially conforms to the shape of the structure 56 outside bone, when in an open air environment. This allows the physician to select in an open air environment a structure having an expanded shape desired to meet the targeted therapeutic result, with the confidence that the expanded shape inside bone will be similar in important respects.

An optimal degree of shaping can be achieved by material selection and by special manufacturing techniques, e.g., thermoforming or blow molding, as will be described in greater detail later.

In some instances, it may not be necessary or desired for the structure to predictably deform and/or assume a desired shape during expansion inside bone. Rather, it may be preferred that the structure expand in a substantially uncontrolled manner, rather than being constrained in its expansion. For example, where compaction of weaker sections of the cancellous bone is desired, it may be preferred that the structure initially expand towards weaker areas within the bone. In such cases, the structure can be formed without the previously-described shape and/or size, and the expanded shape and/or size of the structure can be predominantly determined by the morphology and geometry of the treated bone.

3. Toughness Property

A third desired property for the structure 56, either alone or in combination with one or more of the other described properties, is the ability to resist surface abrasion, tearing, and puncture when in contact with cancellous bone. This property can be characterized in various ways.

One way of measuring a material's resistance to abrasion, tearing and/or puncture is by a Taber Abrasion test. A Taber Abrasion test evaluates the resistance of a material to abrasive wear. For example, in a Taber Abrasion test configured with an H-18 abrasive wheel and a 1 kg load for 1000 cycles (ASTM Test Method D 3489), Texin® 5270 material exhibits a Taber Abrasion value of approximately 75 mg loss. As another example, under the same conditions Texin® 5286 material exhibits a Taber Abrasion value of approximately 30 mg loss. Typically, a lower Taber Abrasion value indicates a greater resistance to abrasion. Desirably, one embodiment of the structure will comprise material having a Taber Abrasion value under these conditions of less than approximately 200 mg loss. More desirably, the structure will comprise material having a Taber Abrasion value under these conditions of less than approximately 145 mg loss. Most desirably, the structure will comprise material having a Taber Abrasion value under these conditions of less than approximately 90 mg loss. Of course, materials having a Taber Abrasion value of greater than or equal to 200 mg loss may be utilized to accomplish some or all of the objectives of the present invention.

Another way of measuring a material's resistance to abrasion, tearing and/or puncture is by Elmendorf Tear Strength. For example, under ASTM Test Method D 624, Texin® 5270 material exhibits a Tear Strength of 1,100 lb-ft/in. As another example, under the same conditions, Texin 5286 exhibits a Tear Strength of 500 lb-ft/in. Typically, a higher Tear Strength indicates a greater resistance to tearing. Desirably, an alternate embodiment of the structure will comprise material having a Tear Strength under these conditions of at least approximately 150 lb-ft/in. More desirably, the structure will comprise material having a Tear Strength under these conditions of at least approximately 220 lb-ft/in. Most desirably, the structure will comprise material having a Tear Strength under these conditions of at least approximately 280 lb-ft/in. Of course, materials having a Tear Strength of less than or equal to 150 lb-ft/in may be utilized to accomplish some or all of the objectives of the present invention.

Another way of measuring a material's resistance to abrasion, tearing and/or puncture is by Shore Hardness. For example, under ASTM Test Method D 2240, Texin® 5270 material exhibits a Shore Hardness of 70 D. As another example, under the same conditions, Texin® 5286 material exhibits a Shore Hardness of 86 A. Typically, a lower Shore Hardness number on a given scale indicates a greater degree of elasticity, flexibility and ductility. Desirably, another alternate embodiment of the structure will comprise material having a Shore Hardness under these conditions of less than approximately 75 D. More desirably, the structure will comprise material having a Shore Hardness under these conditions of less than approximately 65 D. Most desirably, the structure will comprise material having a Shore Hardness under these conditions of less than approximately 100 A. Of course, materials having a Shore Hardness of greater than or equal to 75 D may be utilized to accomplish some or all of the objectives of the present invention.

It should also be noted that another alternate embodiment of a structure incorporating a plurality of materials, such as layered materials and/or composites, may possess significant resistance to surface abrasion, tearing and puncture. For example, a layered expandable structure incorporating an inner body formed of material having a Taber Abrasion value of greater than 200 mg loss and an outer body having a shore hardness of greater than 75 D might possess significant resistance to surface abrasion, tearing and puncture. Similarly, other combinations of materials could possess the desired toughness to accomplish the desired goal of compressing cancellous bone and/or moving cortical bone prior to material failure.

4. Creating a Pre-Formed Structure

The expansion and shape properties just described can be enhanced and further optimized for compacting cancellous bone by selecting an elastomer material, which also possess the capability of being preformed, i.e., to acquire a desired shape by exposure, e.g., to heat and pressure, e.g., through the use of conventional thermoforming or blow molding techniques. Candidate materials that meet this criteria include polyurethane, silicone, thermoplastic rubber, nylon, and thermoplastic elastomer materials.

As described earlier, in the illustrated embodiment, TEXIN® 5286 polyurethane material is used. This material is commercially available from Bayer in pellet form. The pellets can be processed and extruded in a tubular shape. The tubular extrusion can then be cut into individual lengths for further processing. The structure 56 can be formed by exposing a cut tube length to heat and then enclosing the heated tube 60 within a mold while positive interior pressure is applied to the tube length, as is well known in the art.

Further details of the manufacture of a structure suitable for use with the present invention can be found in U.S. patent application Ser. No. 09/420,529, filed Oct. 19, 1999, and entitled "Expandable Preformed Structures for Deployment in Interior Body Regions," which is incorporated herein by reference.

B. Assembly of the Tool

The outer catheter body 16, middle catheter body 20, and inner catheter body 18 can each comprise extruded tubing made, e.g., from TEXIN® 5270. Material. The TEXIN® material can be purchased in pellet form from Bayer. The catheter bodies 16, 18, and 20 can be extruded in a tubular shape. Representative process settings for the extrusions can be found in U.S. patent application Ser. No. 09/420,529, filed Oct. 19, 1999, and entitled "Expandable Preformed Structures for Deployment in Interior Body Regions," which is incorporated herein by reference.

In assembling the tool 48, the proximal end of the structure 56 is bonded to the distal end of the middle catheter body 20 (as FIG. 6 shows) through heat bonding or the use of a suitable adhesive. The middle catheter body 20 and outer catheter body 16 are cut to a desired final length, e.g., which in a representative embodiment is approximately 350 mm measured from the center of the structure 56. The outer catheter body 16 is slid over the middle catheter body 20, from the proximal end toward the distal end. The proximal and distal ends of the catheter bodies 16 and 20 are then bonded together (as FIG. 7 shows).

A suitable UV adhesive (e.g., Dymax 204 CTH, available commercially from Dymax Corp) is applied to the joined proximal ends of the outer catheter body 16 and middle catheter body 20. The joined ends are inserted into the luer fitting 22 of the handle 14 (as FIG. 7 shows). The adhesive joint is cured, e.g., under UV light for an appropriate time period, e.g., 15 seconds. This secures the outer catheter body 16 and middle catheter body 20 to the handle 14.

The distal end of the inner catheter body 18 is flared slightly (as FIG. 6 shows), using, e.g., a 0.075" flare tool. The inner catheter body 18 is inserted, proximal end first, through the distal end of the structure 56. The inner catheter body passes through the middle catheter body 20 and into the luer fitting 30 on the y-shaped adapter/handle 14 (as FIG. 7 shows).

The flared distal end of the inner catheter body 18 is heat bonded to the distal end of the structure 56 (as FIG. 6 shows). The flare tool is desirably kept in place during the heat bonding process, to prevent collapse of the flared distal end.

The proximal end of the inner catheter body 18 is cut to size, if necessary, and is secured to the luer fitting 30 using adhesive (as FIG. 7 shows).

In one embodiment, the distal end of the stylet 52 is bent into a hook shape 60 (see FIG. 6). The unbent proximal end of the stylet 52 is passed through the flared distal end of the inner catheter body 18, until the bent distal end 60 occupies the flared distal end. An adhesive is applied into the flared distal end of the inner catheter body 18. The adhesive closes the distal end of the inner catheter body 18 and bonds the bent distal end 60 of the stylet 52 to the distal end of the inner catheter body 18, which is itself bonded to the distal end of the structure 56. Alternatively, the distal end of the inner catheter body 18 could be heat bonded to the hook shaped end 60 of the stylet 52.

The proximal end of the stylet 52, which extends outside the proximal end of the fitting 30, is cut to size and also bent into a hook shape 62 (see FIG. 7). The bent proximal end 62 is bonded to the luer cap 24 by adhesive (see FIG. 7).

This completes the assembly of the tool 48. The tool 48 can then be packaged for sterilization in a suitable kit.

If desired, the middle and outer catheter bodies 20 and 16 could comprise a single catheter body having sufficient torsional strength to accomplish the objectives of the present invention. For example, the proximal end of the structure 56 and the distal end of the luer fitting 22 could be secured to a hollow hypodermic tube of sufficient diameter to accommodate the inner catheter body 18 and stylet 52. Such a catheter body, comprised of a medical material such as stainless steel or plastic, would have sufficient rigidity to withstand the torsional forces described herein and accomplish the objectives of the present invention.

In another alternative embodiment, the middle and outer catheter bodies 20 and 16 can be designed to deform and/or fail at or below the torsional failure point of the structure 56. For example, where the structure 56 can withstand a torsional force of at least ten ft-lbs before failure, the middle and outer catheter bodies 20 and 16 can be designed to together withstand a maximum of ten ft-lbs before experiencing significant deformation and/or failure. By designing the catheter bodies to deform and/or fail before the structure, the potential for a complete radial tear and/or fragmentation of the structure is significantly reduced and/or eliminated. Moreover, even when the middle and outer catheter bodies 20 and 16 completely fail and separate, the tool 48 retains significant structural integrity to be safely withdrawn from the patient.

Representative other details for the assembly of the catheter bodies 16, 18, and 20, the stylet 52, and the handle 14 can be found in U.S. patent application Ser. No. 09/420,529, filed Oct. 19, 1999, and entitled "Expandable Preformed Structures for Deployment in Interior Body Regions," which is incorporated herein by reference.

III. Use of the Tool

A. Deployment in a Vertebral Body

The structure 56 is well suited for insertion into bone in accordance with the teachings of U.S. Pat. Nos. 4,969,888, 5,108,404, 5,827,289, and 5,972,015, which are incorporated herein by reference.

Figure 11:
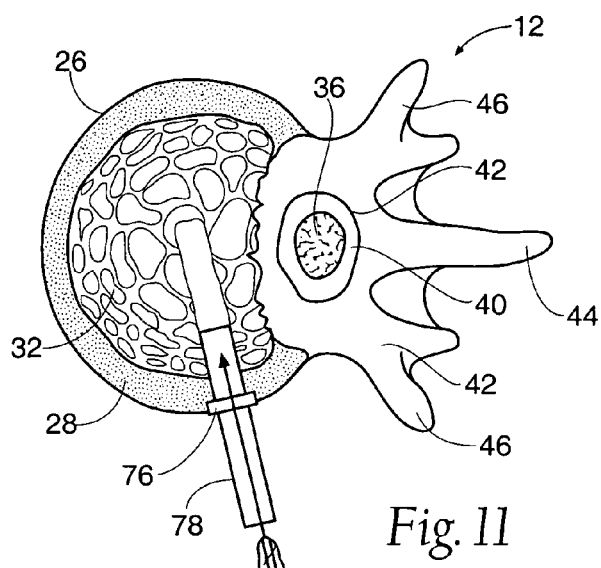
FIG. 11 is a coronal view of the vertebral body shown in FIG. 1, with the expandable structure of the tool shown in FIG. 3 placed in a fully wrapped, low profile condition, ready for deployment through a cannula into the interior of the vertebral body.

For example, as FIG. 11 shows, access can be accomplished by drilling an access portal 76 through a side of the vertebral body 26 and partially into cancellous bone inside the vertebral body 26. This is called a lateral approach. Alternatively, the access portal can pass through either pedicle 42, which is called a transpedicular approach, or can along the anterior side of the vertebra. A hand held tool can be used to facilitate formation of the access portal 76, such as disclosed in copending U.S. patent application Ser. No. 09/421,635, filed Oct. 19, 1999, and entitled "Hand Held Instruments that Access Interior Body Regions." Another hand held tool that can be used to form the access portal 76 and gain access is disclosed in copending U.S. patent application Ser. No. 09/014,229 filed Jan. 27, 1998 and entitled "A Slip-Fit Handle for Hand-Held Instruments that Access Interior Body Regions."

A guide sheath or cannula 78 is placed into communication with the access portal 76, which can comprise a component part of the hand held tool just described.

Before advancement through the cannula 78, the luer cap 24 is rotated, as previously described, to wrap the structure 56 about the distal end of the inner catheter body 18 and stylet 52, as FIG. 11 shows.

The wrapping efficiently "packs" the structure 56 into a cylindrical shape, to significantly reduce the cross-sectional profile of the structure 56 during its insertion through the cannula 78. Moreover, the wrapping uniformly distributes the structure 56 about the inner catheter body 18. Structures 56 having desired enlarged external diameters to achieve greater compaction of cancellous bone, can, before deployment into bone, be twisted down to significantly smaller external diameters for deployment into bone through smaller diameter cannulas. This, in turn, enables smaller incisions and less invasive procedures.

Once the structure 56 has been twisted in one direction, e.g., clockwise, for passage through the cannula 78 (by rotation of the luer cap 24), the physician can chose to twist the entire catheter tube assembly 10 as it advances through the cannula 78 in the opposite direction, i.e., counterclockwise, which will desirably further reduce the profile of the structure 56.

Moreover, because the material of the structure 56 is twisted against the inner catheter body 18 and stylet 52, the normal force exerted by the walls of the cannula 78 against the structure 56 is reduced. Accordingly, the low profile offers clearance between the structure 56 and the cannula walls and desirably reduces the overall frictional drag on the structure. The twisted structure 56 passes readily through the cannula 78, without back pressure. Material wear or damage to the structure 56 caused by frictional forces can also be minimized.

In addition to reducing the profile of the structure 56 for insertion through the cannula 78, the resultant twisting of the structure 56 also evenly tightens or "packs" the structure material against the inner catheter body 18 and stylet 52. This overall tightening of material significantly reduces, and can essentially eliminate, the possibility that the material of the structure 56 can slide or "bunch-up" as the structure 56 travels down the cannula 76. This outcome further reduces the frictional forces associated with passage of the structure 56 through the cannula 76 and/or the potential for damage to the structure 56 occasioned by the passage.

The presence of the stylet 52 and the middle catheter body 20 also adds significant torsional rigidity to the catheter tube assembly 10 of the tool 48. The increased torsional rigidity enables the physician to increase the twisting pressure that can be imparted to the tool 48 during insertion into and removal from the targeted interior bone region. For example, if the structure 56 meets an obstruction during deployment or removal, the increased torsional rigidity, column strength and yield strength of the catheter tube assembly 10 permits the physician to twist and/or push and/or pull the structure 56 past the obstruction and/or move the obstruction.

Furthermore, the presence of the bent distal end 62 of the stylet 52 at the distal end of the inner catheter tube 18 enhances the torsional strength of the bond between the catheter tube assembly 10 and the structure 56. This can significantly increase the amount of torque that can be transmitted by the luer cap 24 via the stylet 52 to twist the distal end of the structure 56. The twisting of the structure 56 itself imparts significantly more rigidity to the distal end of the catheter tube assembly 10. This allows the physician to use the twisted structure 56 itself to push or pull aside obstructions.

The presence of the stylet 52 also further facilitates passage of the structure 56 through the cannula 78 by "pushing" the distal end of the structure through the cannula 78 and the cancellous bone 32. Because the stylet has significant column strength, as the physician "pushes" the tool 48 through the cannula 78, this axial force is transmitted through the stylet 52 to the closed distal end of the structure 56. The remainder of the structure 56 is then essentially "pulled" behind the distal end. If the structure becomes wedged or caught within the cannula 78, the "pulling" action of the distal end will typically cause the structure 56 to extend longitudinally, thinning the structure 56 and desirably freeing the obstruction.

As FIG. 11 shows, the catheter tube assembly 10 is advanced through the cannula 78 with the structure 56 wrapped in a low profile condition. The structure 56 is deployed into contact with cancellous bone 32 inside the vertebral body 12. Access in this fashion can be accomplished using a closed, minimally invasive procedure or with an open procedure.

Figure 12:
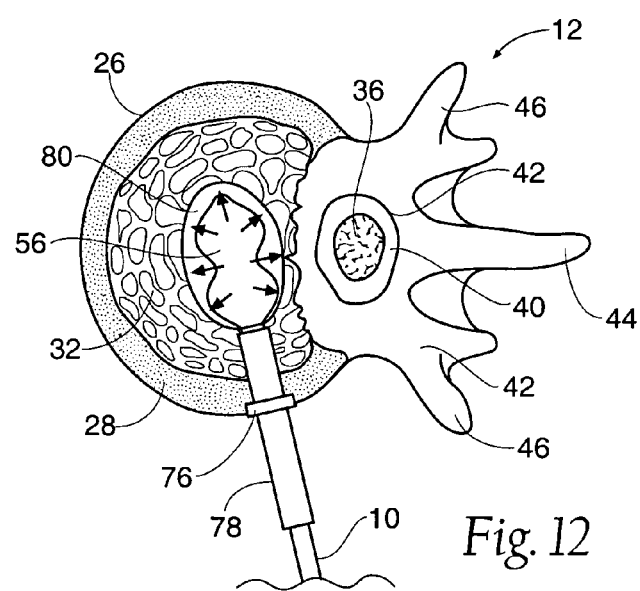
FIG. 12 is a coronal view of the vertebral body shown in FIG. 11, with the expandable structure of the tool shown in a fully deployed and expanded condition to compress cancellous bone and form a cavity.

Once deployed inside bone, the luer cap 24 can be rotated in an opposite direction to unwrap the structure 56 for use. As FIG. 12 shows, subsequent expansion of the structure 56 (indicated by arrows in FIG. 12) compresses cancellous bone 32 in the vertebral body 26. The compression forms an interior cavity 80 in the cancellous bone 32. As previously noted, the structure can alternatively be used to displace cortical bone directly, with or without concurrent compression of cancellous bone.

After the cavity 80 is formed in the vertebral body and/or cortical bone is displaced to a desired position, it is also desirable to reduce the size of the structure 56 so that it can be withdrawn from the vertebral body 12. In prior arrangements, the physician releases the pressure of the inflation fluid and draws a suction on the structure 56, trying to reduce the cross sectional profile as much as possible to facilitate removal through the cannula 78. However, should the structure 56, during use, develop pinhole leaks or tears or otherwise experience damage, it can be difficult to draw and/or maintain a vacuum within the structure 56, as bodily fluids or air can enter the compromised structure 56.

The ability to mechanically impart a low profile after use, by twisting the structure 56, allows the profile of even a compromised structure 56 to be reduced for removal through the cannula 78. Size reduction by twisting can even obviate the absolute need for a strong vacuum, although it should be realized that the most efficient size reduction is ideally achieved when a vacuum is drawn and the structure 56 is then twisted.

Furthermore, expansion of the collapsed size of the structure 56, occasioned by plastic deformation and/or stretching of the structure material during cavity formation, can be accommodated by twisting the extra, stretched material up against the inner catheter body 18. In this manner, all material will be desirably wrapped against the inner catheter body 18, preventing the structure 56 from "bunching up," which can inhibit withdrawal of the catheter tube assembly 10.

Since both the inner catheter body 18 and the stylet 52 are attached directly to the distal bond of the structure 56, the overall pull strength of the catheter tube assembly 10 is also increased. The pull strength is further enhanced by the presence of the bent end 62 of the stylet 52 bonded within the distal bond of the structure 56. This further increases the magnitude of the force a physician can use to pull the structure 56 out of the vertebral body. Even if a complete failure of the bond occurs during use at the proximal end of the structure 56, or even if the structure 56 experiences a complete radial tear during use, the presence of the enhanced bond at the distal end of the structure 56 makes it still possible to retrieve the entire damaged structure 56 by pulling on the catheter tube assembly 10.

Figure 16:
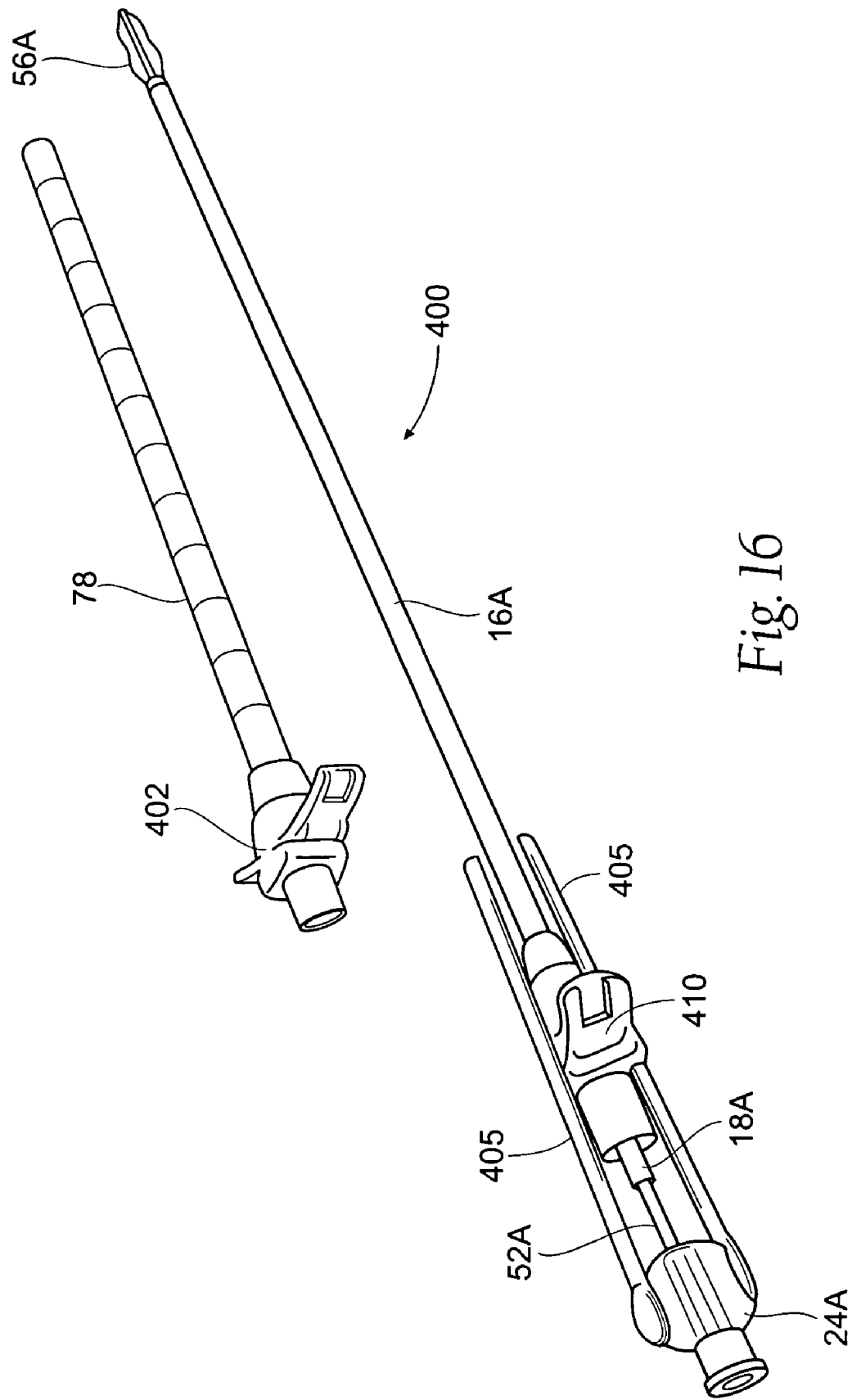
FIG. 16 is a perspective view of an alternate embodiment of a tool which carries at its distal end an expandable structure that embodies features of the invention.

FIG. 16 depicts an alternate embodiment of a catheter tube assembly 400 constructed in accordance with the teachings of the present invention. Because many of the features in this embodiment are similar to components previously described, like reference numerals will be used to describe similar components.

Catheter tube assembly 400 comprises an outer catheter body 16A, an inner catheter tube 18A and a stylet 52A which extends through the outer and inner catheter bodies. The proximal end of an expandable structure 56A is attached to the distal end of the outer catheter body 16A, and the distal end of the expandable structure 56A is secured to the distal end of the inner catheter tube 18A and stylet 52A. The proximal end of the stylet 52A is desirably attached to a cap 24A. One or more struts 405, extending along the outer catheter body 16A, are attached at a proximal end to the cap 24A.

A handle 410 is secured to the proximal end of the outer catheter body 16A. The proximal end of the inner catheter tube 18A is desirably secured within the handle 410 at a location proximal to an inflation port 38A.

Desirably, the inner catheter tube 18A and stylet 52A are slidable relative to the outer catheter body 16A. Because the ends of the structure 56 are bonded to the inner catheter tube/stylet and the outer catheter tube, however, longitudinal displacement of the stylet 52A and inner catheter tube 18A will cause the structure 56A to stretch or contract. When the handle 410 is drawn towards the cap 24A, therefore, the outer catheter body 16A slides along the inner catheter body/stylet and draws the proximal end of the structure 56A towards the cap 24A, which stretches the structure 56A longitudinally, reducing its outer profile. When the handle 410 is released, the structure will typically attempt to regain its original shape, thereby drawing the handle 410 away from the cap 24A towards its original resting position.

In use, the physician is able to use a single hand to draw the handle 410 towards the cap 24A, reducing the outer profile of the structure 56A for insertion through a cannula 78. The structure is then advanced through the cannula 78 in this reduced profile condition. Once the structure 56A enters the vertebral body, the handle 410 may be released, allowing the structure 56A to assume its original shape. The structure can then be utilized as previously described.

It should be understood that varying degrees of force may be imparted to the handle 410 to extend the structure 56A to a desired degree. For example, in the disclosed embodiment, a force of 4 ounces will extend the structure approximately ³⁄₁₆". Similarly, a force of 3 pounds will extend the structure approximately ½". Desirably, a force of at least approximately ½ ounce will extend the structure to a useful degree. More desirably, a force of at least approximately 2 ounces will extend the structure to a useful degree. Even more desirably, a force of at least approximately 8 ounces will extend the structure to a useful degree. Most desirably, a force of at least approximately a 1 pound will extend the structure to a useful degree.

Figure 17:
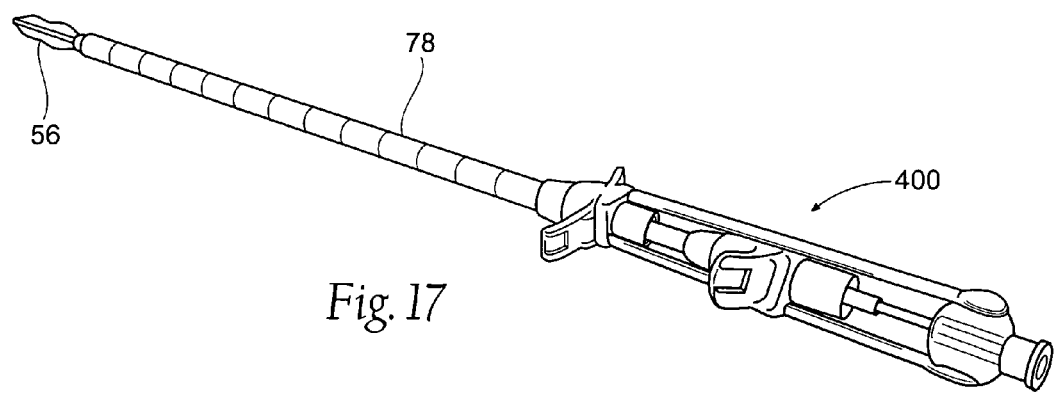
FIG. 17 is a perspective view of the tool of FIG. 16, with the tool inserted through a cannula.
Figure 18:
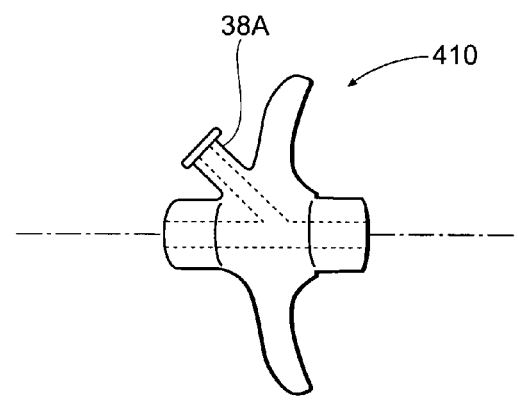
FIG. 18 is a side plan view of a handle suitable for use with the tool of FIG. 16.
Figure 19:
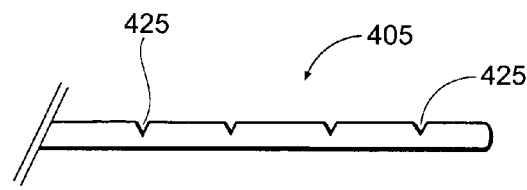
FIG. 19 is a partial plan view of one embodiment of a strut incorporating features of the invention.

The disclosed embodiment further includes a stop which inhibits and/or prevents the assembly 400 from advancing beyond a predetermined distance into the vertebral body (not shown). In this embodiment, as the assembly 400 is advanced to a desired position within the vertebral body, the distal ends of the struts 405 will desirably contact one or more contact surfaces 402 on the cannula 78, thereby preventing further advancement of the assembly 400 through the cannula 78. (See FIG. 17). Because the struts 405 are connected to the stylet 52A, and the stylet 52A extends to the distal end of the structure 56, the maximum penetration depth of the assembly 400 can be controlled. Even where the profile of the structure 56 has been reduced, the struts 405 will prevent the distal tip of the stylet 52A from advanced further than a predetermined depth.

If deeper penetration of the vertebral body is desired, the struts 405 may be shortened by the physician, permitting the assembly 400 to extend further into the vertebral body. To facilitate such alterations, the struts 405 can comprise one or more ridges, notches or grooves 425 at predetermined locations, creating desired fracture lines along the strut 405 and allowing the physician to quickly and easily shorten the struts 405 to a desired length using appropriate tools such as surgical scissors, clamps and/or various other types of cutting tools.

Figure 13:
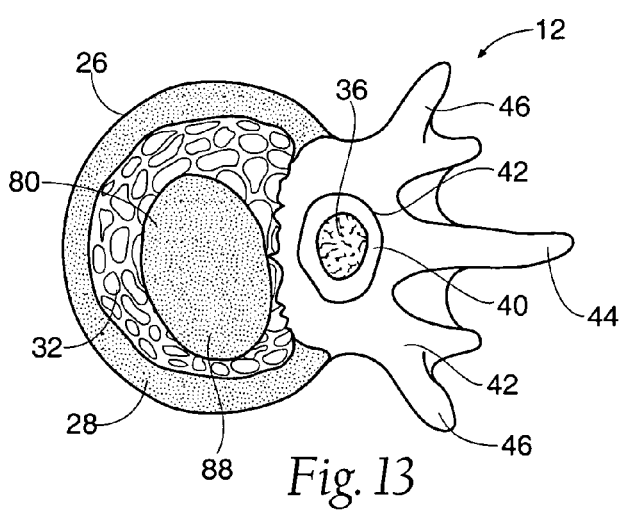
FIG. 13 is a coronal view of the vertebral body shown in FIG. 12, upon removal of the tool, showing the cavity formed by the compression of cancellous bone by the expandable structure.

As FIG. 13 shows, subsequent collapse and removal of the structure 56 leaves the cavity 80 in a condition to receive a filling material 88, e.g., bone cement, allograft tissue, autograft tissue, hydroxyapatite, granular bone material such as ProOsteon™, demineralized bone matrix such as Grafton™ or SRS™ calcium phosphate cement, Collagraft™ or synthetic bone substitute. Alternatively, the material could comprise a compression-resistant material such as rubber, polyurethane, cyanoacrylate, silicone rubber, or metal. The material could also comprise a semi-solid slurry material (e.g., a bone slurry in a saline base). Alternatively, the material could comprise stents, reinforcing bar (Re-Bar) or other types of internal support structures, which desirably resist compressive forces acting on the bone and/or filler material. The material 88 desirably provides improved interior structural support for cortical bone 32.

The filling material may also comprise a medication, or a combination of medication and a compression-resistant material, as described above. Alternatively, the material can comprise a bone filling material which does not withstand tensile, torsional and/or compressive forces within the cavity. For example, where the patient is not expected to experience significant forces within the spine immediately after surgery, such as where the patient is confined to bed rest or wears a brace, the filling material need not be able to immediately bear tensile, torsional and/or compressive loads. Rather, the filling material could provide a scaffold for bone growth, or could comprise a material which facilitates or accelerates bone growth, allowing the bone to heal over a period of time. As another alternative, the filling material could comprise a resorbable or partially-resorbable source of organic or inorganic material for treatment of various bone or non-bone-related disorders including, but not limited to, osteoporosis, cancer, degenerative disk disease, heart disease, acquired immune deficiency syndrome (AIDS) or diabetes. In this way, the cavity and/or filler material could comprise a source of material for treatment of disorders located outside the treated bone.

The compaction of cancellous bone 32, as shown in FIG. 12, can also exert an interior force upon the surrounding cortical bone 28. The interior force can elevate or push broken and compressed bone back to or near its original prefracture, or other desired, condition. In the case of a vertebral body 26, deterioration of cancellous bone 32 can cause the top and bottom plates (designated TP and BP in FIG. 2), as well as the side walls (designated AW and PW in FIG. 2), to compress, crack, or move closer together, reducing the normal physiological distance between some or all of the plates. In this circumstance, the interior force exerted by the structure 56 as it compacts cancellous bone 32 moves some or all of the plates and/or walls farther apart, to thereby restore some or all of the spacing between them, which is at or close to the normal physiological distance. As previously described, the structure can alternately be used to directly displace cortical bone, with or without concurrent compaction of cancellous bone.

There are times when a lesser amount of cancellous bone compaction is indicated. For example, when the bone disease being treated is localized, such as in avascular necrosis, or where local loss of blood supply is killing bone in a limited area, an expandable structure 56 can compact a smaller volume of total bone. This is because the diseased area requiring treatment is smaller.

Another exception lies in the use of an expandable structure 56 to improve insertion of solid materials in defined shapes, like hydroxyapatite and components in total joint replacement. In these cases, the structure shape and size is defined by the shape and size of the material being inserted.

Yet another exception lies in the use of expandable structures in bones to create cavities to aid in the delivery of therapeutic substances, as disclosed in copending U.S. patent application Ser. No. 08/485,394, previously mentioned. In this case, the cancellous bone may or may not be diseased or adversely affected. Healthy cancellous bone can be sacrificed by significant compaction to improve the delivery of a drug or growth factor which has an important therapeutic purpose. In this application, the size of the expandable structure 56 is chosen by the desired amount of therapeutic substance sought to be delivered.

It should be understood that the filling material 88 itself could be used to expand the structure 56 within the vertebral body 26, thereby causing compaction of the cancellous bone 32 and/or movement of the cortical bone 28 as previously described. If desired, the filling material 88 within the structure 56 could be allowed to harden, and the structure 56 and hardened filling material 88 could remain within the vertebral body 26. This would significantly reduce the possibility of non-hardened filling material 88 leaking outside of the vertebral body 26. Alternatively, the pressurized fluid could be withdrawn from the structure 56 after formation of some or all of the cavity 80, and filler material 88 could be injected into the structure to fill the cavity 80 and/or complete expansion of the structure 56. As another alternative, filler material 88 could be used to expand the structure 56, and the structure 56 could subsequently be removed from the vertebral body 26 before the filling material 88 within the vertebral body 26 sets to a hardened condition. If desired, the structure 56 can be made from an inert, durable, non-degradable plastic material, e.g., polyethylene and other polymers. Alternatively, the structure 56 can be made from a bio-absorbable material, which degrades over time for absorption or removal by the body. As another alternative, the filling material could comprise a two-part material including, but not limited to, settable polymers or calcium alginate. If desired, one part of the filling material could be utilized as the expansion medium, and the second part added after the desired cavity size is achieved.

The structure can also be made from a permeable, semi-permeable, or porous material, which allows the transfer of filling material and/or medication contained in the filling material into contact with cancellous bone through the wall of the structure. If desired, the material can comprise a membrane that allows osmotic and/or particulate transfer through the material, or the material can comprise a material that allows the medication to absorb into and/or diffuse through the material. Alternatively, medication can be transported through a porous wall material by creating a pressure differential across the wall of the structure. As another alternative, fluids, cells and/or other materials from the patient's body can pass and/or be drawn through the material into the structure for various purposes including, but not limited to, bone ingrowth, fluid/cellular analysis, bone marrow harvesting, and/or gene therapy (including gene replacement therapy).

The features of the invention are set forth in the following claims.

We claim:

1. A method for treating bone comprising:
   providing a tubular assembly comprising a first tubular member having a distal end, a second tubular member extending along an axis, longitudinally extending through the interior of the first tubular member, and having a distal end projecting outwardly beyond the distal end of the first tubular member, and a torque transmitting stylet longitudinally extending through the interior of the second tubular member and having a distal end fixedly and nonremovably secured to the distal end of the second tubular member,
   providing a structure having opposite ends spaced along the axis, the structure being adapted to undergo expansion outwardly about the axis, the structure having a normally unwrapped condition having an outside diameter,
   securing one end of the structure to the distal end of the first tubular member, and the other end of the structure to the outwardly projecting distal end of the second tubular member, in a manner such that the structure substantially envelopes the outwardly projecting distal end of the second tubular member,
   placing the structure in a wrapped condition by rotating the stylet to thereby rotate the second tubular member relative to the first tubular member and wrap the structure inwardly about the outwardly projecting distal end of the second tubular member to reduce the outside diameter,
   inserting the structure, while in the wrapped condition, into bone,
   returning the structure to the unwrapped condition inside bone, and
   causing expansion of the structure in cancellous bone.

2. A method according to claim 1 further including introducing a material into the bone.

3. A method according to claim 1 wherein the expansion compacts cancellous bone.

4. A method according to claim 1 wherein the expansion forms a cavity in cancellous bone.

5. A method according to claim 4 further including filling the cavity with a material.

6. A method according to claim 5 wherein the material comprises bone cement.

7. A method according to claim 5 wherein the material comprises synthetic bone substitute.

8. A method according to claim 5 wherein the material comprises a flowable material that sets to a hardened condition.

9. A method according to claim 1 further including, after the expansion, reducing the size of the structure for removal from the bone.

10. A method according to claim 9 wherein the reducing includes placing the structure in the wrapped condition.

11. A method according to claim 1 wherein the wrapping includes causing differential rotation of one end of the structure about the axis relative to the other end.

12. A method according to claim 1 wherein expansion moves cortical bone.

13. A method according to claim 1 wherein the stylet is of a generally flexible construction.

14. A method according to claim 1 further comprising causing the structure to axially elongate in response to rotation of the stylet.

15. A method according to claim 1 wherein the step of providing a tubular assembly is performed in a manner such that an annular flow passage communicating with the interior of the structure is created between the first and second tubular members, and wherein the step of causing expansion of the structure in cancellous bone is performed by flowing an expansion fluid through the annular flow passage into the interior of the structure.

* * * * *